US009981904B2

(12) United States Patent
Wigbers et al.

(10) Patent No.: US 9,981,904 B2
(45) Date of Patent: May 29, 2018

(54) PROCESS FOR PREPARING PRIMARY AMINES USING AN UNSUPPORTED COBALT CATALYST

(71) Applicant: BASF SE, Ludwigshafen (DE)

(72) Inventors: Christof Wilhelm Wigbers, Lich (DE); Wolfgang Maegerlein, Limburgerhof (DE); Thomas Krug, Worms (DE); Johann-Peter Melder, Boehl-Iggelheim (DE); Thomas Heidemann, Viernheim (DE); Bernd Stein, Alsbach-Haehnlein (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/505,803

(22) PCT Filed: Aug. 25, 2015

(86) PCT No.: PCT/EP2015/069460
§ 371 (c)(1),
(2) Date: Feb. 22, 2017

(87) PCT Pub. No.: WO2016/030383
PCT Pub. Date: Mar. 3, 2016

(65) Prior Publication Data
US 2017/0275232 A1 Sep. 28, 2017

(30) Foreign Application Priority Data
Aug. 28, 2014 (EP) ..................................... 14182673

(51) Int. Cl.
C07C 209/48 (2006.01)
B01J 23/75 (2006.01)
(Continued)

(52) U.S. Cl.
CPC ............. C07C 209/48 (2013.01); B01J 23/75 (2013.01); B01J 23/78 (2013.01); B01J 35/002 (2013.01);
(Continued)

(58) Field of Classification Search
None
See application file for complete search history.

(56) References Cited

U.S. PATENT DOCUMENTS 4,598,058 A 7/1986 Frank et al.
5,132,427 A 7/1992 Koehler et al.
(Continued)

FOREIGN PATENT DOCUMENTS

DE 34 03 377 A1 8/1985
EP 0 424 738 A2 5/1991
(Continued)

OTHER PUBLICATIONS

International Search Report dated Dec. 4, 2015 in PCT/EP2015/069460.
(Continued)

Primary Examiner — Clinton A Brooks
(74) Attorney, Agent, or Firm — Oblon, McClelland, Maier & Neustadt, L.L.P.

(57) ABSTRACT

The invention relates to a process for preparing primary amines, which comprises hydrogenating at least one nitrile in an apparatus (V1) in the presence of an unsupported cobalt catalyst to obtain at least one primary amine, with recurrent or continuous addition of at least one compound (I) to the apparatus (V1), said compound (I) comprising at least one component selected from alkali metal, alkaline earth metal and rare earth metal.

21 Claims, 5 Drawing Sheets

Figure 1:
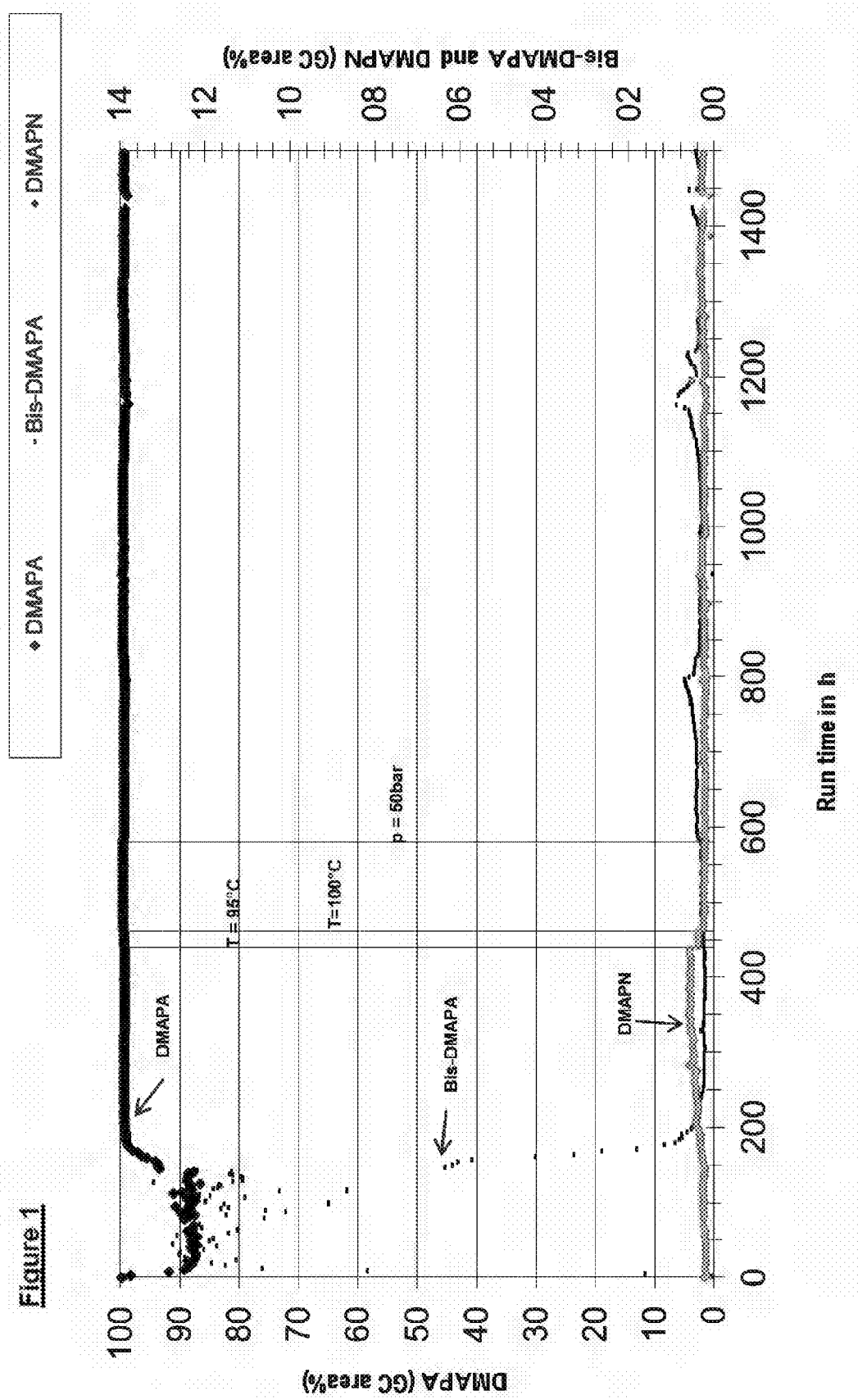

(51) Int. Cl.
*B01J 37/18* (2006.01)
*B01J 35/00* (2006.01)
*B01J 23/78* (2006.01)

(52) U.S. Cl.
CPC .......... *B01J 35/0006* (2013.01); *B01J 37/18* (2013.01); *C07C 2523/75* (2013.01)

(56) References Cited

U.S. PATENT DOCUMENTS

| | | |
|---|---|---|
| 5,254,738 A | 10/1993 | Koehler et al. |
| 5,536,691 A | 7/1996 | Breitscheidel et al. |
| 5,696,048 A | 12/1997 | Breitscheidel et al. |
| 5,869,653 A | 2/1999 | Johnson |
| 2001/0003136 A1 | 6/2001 | Nouwen et al. |
| 2004/0149314 A1 | 8/2004 | Cha et al. |
| 2005/0159624 A1 | 7/2005 | Goeboeloes et al. |
| 2008/0214871 A1 | 9/2008 | Ernst et al. |
| 2011/0313188 A1 | 12/2011 | Wigbers et al. |
| 2016/0009633 A1 | 1/2016 | Luyken et al. |

FOREIGN PATENT DOCUMENTS

| | | |
|---|---|---|
| EP | 0 636 409 A1 | 2/1995 |
| EP | 0 445 589 B1 | 5/1995 |
| EP | 0 742 045 A1 | 11/1996 |
| EP | 0 913 388 A1 | 5/1999 |
| EP | 0 963 975 A1 | 12/1999 |
| EP | 1 106 600 A2 | 6/2001 |
| FR | 1.530.809 A | 6/1968 |
| WO | WO 03/070688 A1 | 8/2003 |
| WO | WO 2006/077233 A1 | 7/2006 |
| WO | WO 2007/104663 A1 | 9/2007 |
| WO | WO 2010/089346 A2 | 8/2010 |
| WO | WO 2015/150489 A1 | 10/2015 |
| WO | WO 2016/030372 A1 | 3/2016 |

OTHER PUBLICATIONS

International Preliminary Report on Patentability and Written Opinion dated Mar. 9, 2017 in PCT/EP2015/069460.
Gerhart Eigenberger "Fixed-Bed Reactors" Ullmann's Encyclopedia of Industrial Chemistry, vol. 15, DOI: 10.1002/14356007. b04_199, Jun. 15, 2000, pp. 14-52 with cover page.
G. Ertl, et al., "Handbook of Heterogeneous Catalysis" VCH Weinheim, vol. 1, 1997, pp. 98-99 with cover pages.

PROCESS FOR PREPARING PRIMARY AMINES USING AN UNSUPPORTED COBALT CATALYST

The present invention relates to a process for preparing primary amines, wherein a nitrile is hydrogenated in the presence of an unsupported cobalt catalyst to obtain the corresponding primary amine. The hydrogenation is conducted in an apparatus (V1), for example in a reactor. Added to this apparatus (V1), especially during the hydrogenation operation, recurrently or continuously is at least one compound (I) based on alkali metals, alkaline earth metals and/or rare earth metals; for example, the compound (I) added is an aqueous lithium hydroxide solution.

In the catalytic hydrogenation of nitriles to primary amines according to the prior art, the unwanted formation of secondary and tertiary amines can be substantially suppressed by the addition of ammonia or alkali metal hydroxides. The catalysts used here frequently comprise iron, cobalt and/or nickel as a main component. For example, adiponitrile, an important nitrile in terms of volume, can be hydrogenated under high-pressure conditions in the presence of elemental iron and ammonia or at moderate pressure in the presence of Raney nickel and sodium hydroxide solution to give hexamethylenediamine. The removal and recycling of ammonia constitutes a not insignificant cost factor for capital and energy costs. This is also true of the hydrogenation of nitrile intermediates, such as isophoronenitrile, acetonitrile and dimethylaminopropionitrile (DMAPN), to the corresponding primary amines.

EP-A 913 388 describes an improved process for hydrogenating nitriles to primary amines, especially dimethylaminopropionitrile (DMAPN) to dimethylaminopropylamine (DMAPA). Hydrogenation is effected in the presence of suspended cobalt sponge catalysts such as Raney cobalt, lithium compounds and water, without addition of ammonia. Prior to the hydrogenation, the Raney cobalt catalyst is treated with 0.1 to 100 mmol of lithium hydroxide per gram of cobalt sponge catalyst. A disadvantage of the procedure of EP-A 913 388 is that the removal of suspension catalysts from hydrogenation outputs and recycling thereof into the hydrogenation is often afflicted with difficulties. The Raney cobalt catalysts described in EP-A 913 388 are not unsupported cobalt catalysts. Because of the specific mode of preparation of these Raney catalysts, they have a very high surface area.

WO 2003/070 688 describes the hydrogenation of nitriles to primary amines in the presence of nickel or cobalt catalysts which have been pretreated ex situ with alkali metal carbonates or alkali metal hydrogencarbonates, preferably potassium carbonate. "Ex situ" is understood to mean that the catalyst has been modified outside and especially prior to the hydrogenation reaction of nitrile to give amine. Suitable catalysts described are especially Raney nickel catalysts; it is optionally also possible to use Raney cobalt catalysts. However, nowhere is there any description of continuous or recurrent pretreatment with the alkali metal compounds actually during the hydrogenation. Moreover, there is no pointer that lithium compounds are also suitable for the purpose.

WO 2007/104 663 A1 also discloses use of lithium-comprising fixed bed cobalt catalysts in the absence of ammonia for the hydrogenation of nitriles to primary amines. Catalysts of this kind can be prepared by reduction of catalyst precursors of the formula $LiCoO_2$ with hydrogen in a solvent such as tetrahydrofuran. Catalyst precursors of this kind are also obtainable by calcining mixtures of lithium salts and cobalt salts, for example lithium carbonate and cobalt carbonate. However, at no point does WO 2007/104 663 disclose that it is possible to recurrently or continuously add a compound (I) such as lithium hydroxide in the course of hydrogenation.

A further disadvantage of the cobalt catalysts which comprise up to 10% by weight of lithium after reduction and are described in WO 2007/104 663 is that water present in the nitrile intended for hydrogenation and hence in the hydrogenation mixture leads to catalyst deactivation. A further disadvantage is that, when $LiCoO_2$ is used as catalyst precursor, up to 10% by weight of lithium is bound within the catalyst without getting to the catalytically active zone in order to become catalytically active therein.

It is an object of the present invention to provide the novel process for preparing primary amines from the corresponding nitriles using a cobalt catalyst.

The object is achieved by a process for preparing primary amines, which comprises hydrogenating at least one nitrile in an apparatus (V1) in the presence of an unsupported cobalt catalyst to obtain at least one primary amine, with recurrent or continuous addition of at least one compound (I) to the apparatus (V1), said compound (I) comprising at least one component selected from alkali metal, alkaline earth metal and rare earth metal.

Through the process of the invention, it is possible to prepare primary amines in an advantageous manner, since unsupported cobalt catalysts, preferably in the form of fixed bed catalysts, are used. This also enables low-pressure hydrogenation of the corresponding nitriles with hydrogen in the liquid phase. The process of the invention additionally features a high activity and service life of the unsupported cobalt catalysts used. Because of the continuous or at least recurrent addition of at least one compound (I), especially in the form of aqueous lithium hydroxide, a high yield and selectivity of the primary amines formed is additionally found. Further advantages of the process of the invention are that the process can also be conducted in the presence of water, especially with use of water-containing nitriles, and that an ammonia-free mode of operation (hydrogenation) is also possible without leading to a significant drop in the nitrile conversion and in the selectivity for primary amines.

A common requirement in the hydrogenation of nitriles to the corresponding amines is to achieve a high conversion based on the nitrile used, since unconverted or only partly converted nitriles can be removed only with difficulty and can lead to unwanted properties in the subsequent applications, such as odor and discoloration.

The advantage of the present invention is thus that the process of the invention enables the hydrogenation of nitriles at high conversions in high selectivity and yield over long reaction times. Moreover, the formation of unwanted by-products such as secondary amines is reduced.

This makes it possible to conduct the hydrogenation under milder reaction conditions, especially at lower pressure and/or at lower temperature.

Thus, the present invention enables an economically viable process for hydrogenation. More particularly, the formation of secondary and tertiary amines, as can arise, for example, through reaction of unconverted amine with partially hydrogenated nitrile (imine intermediate), is reduced.

More particularly, the process of the invention enables the preparation of isophoronediamine with high selectivity and yield. More particularly, it is possible to reduce the content of unwanted isophoronenitrile amine (IPNA). IPNA can form, for example, through reaction of isophoronenitrile with ammonia, which at first reacts to give isophoronenitrile imine, which then reacts preferentially with hydrogen to give isophoronenitrile amine.

The process of the invention likewise preferably serves to prepare 3-(dimethylamino)-propylamine (DMAPA). More particularly, the process of the invention enables a reduction in the content of bis-DMAPA. It is an intermediate which is used, for example, for production of surface-active substances, soaps, cosmetics, shampoos, hygiene products, washing compositions and crop protection compositions. DMAPA is also used for water treatment and as a polymerization catalyst for PU and epoxy.

It is also considered to be an advantage of the process of the invention over prior art processes based on Raney cobalt catalysts in suspension mode that such Raney cobalt catalysts are fundamentally unsuited to use in a fixed bed mode. The installation and deinstallation of these Raney cobalt catalysts should be effected under inert conditions.

The process of the invention is also advantageous over prior art processes based on the use of what are called monolithic catalysts. Compared to the process of the invention using unsupported cobalt catalysts, the use of monolithic catalysts (wherein cobalt is applied to a monolithic shaped body) is significantly costlier in terms of production; the installation of these catalysts into a conventional reactor is likewise more difficult. The use of monolithic catalysts is thus less economic compared to the process of the invention.

The process of the invention is also advantageous over processes based on the use of $LiCoO_2$ catalysts because a loss of activity is observed in the case of the $LiCoO_2$ catalysts with increasing operating time, since lithium leaches out of the corresponding catalyst. This type of catalyst is thus not very suitable for conducting nitrile hydrogenations in the presence of water (leaching effect).

The process of the invention for preparing primary amines using an unsupported cobalt catalyst is defined in detail hereinafter.

In the process of the invention, it is possible in principle to use any nitriles known to those skilled in the art. According to the invention, it is possible to use a single nitrile or else a mixture of two or more nitriles. The nitriles used (reactants) may have one or else more than one nitrile function. According to the invention, the hydrogenation converts the nitrile functions in the nitriles used to the corresponding amine function. Preferably, in accordance with the invention, the corresponding primary amine is prepared from every nitrile used, without any chemical change in other components (functional groups) of the corresponding nitrite.

Preferably, the nitrile is an aliphatic mono-, di- or trinitrile, a cycloaliphatic mono- or dinitrile, an alpha-, beta- or omega-aminonitrile or an alkoxynitrile.

Preference is further given to using aliphatic mono-, di- and/or trinitriles (linear or branched) having 1 to 30 and especially 2 to 18 or 2 to 8 carbon atoms or cycloaliphatic mono- and dinitrile having 6 to 20 and especially 6 to 12 carbon atoms or alpha-, beta- or omega-aminonitriles or alkoxynitriles having 1 to 30 and especially 2 to 8 carbon atoms in the process of the invention.

In addition, it is possible with preference to use aromatic nitriles having 6 to 18 carbon atoms. The abovementioned mono-, di- or trinitriles may be mono- or polysubstituted.

Particularly preferred mononitriles are acetonitrile for preparation of ethylamines, propionitrile for preparation of propylamines, butyronitrile for preparation of butylamines, lauronitrile for preparation of laurylamine, stearyl nitrile for preparation of stearylamine, N,N-dimethylaminopropionitrile (DMAPN) for preparation of N,N-dimethylaminopropylamine (DMAPA), and benzonitrile for preparation of benzylamine.

Particularly preferred dinitriles are adiponitrile (ADN) for preparation of hexamethylenediamine (HMD) and/or 6-aminocapronitrile (ACN), 2-methylglutaronitrile for preparation of 2-methylglutarodiamine, succinonitrile for preparation of butane-1,4-diamine and suberonitrile for preparation of octamethylenediamine.

Particularly preferred cyclic nitriles are isophoronenitrile imine (IPNI) and/or isophoronenitrile (IPN) for preparation of isophoronediamine and isophthalonitrile for preparation of meta-xylylenediamine.

Particularly preferred β-aminonitriles are aminopropionitrile for preparation of 1,3-diaminopropane or addition products of alkylamines, alkyldiamines or alkanolamines onto acrylonitrile. For instance, it is possible to convert addition products of ethylene diamine and acrylonitrile to the corresponding diamines. For example, 3-[2-aminoethyl]aminopropionitrile can be converted to 3-(2-aminoethyl)aminopropylamine, and 3,3'-(ethylenediimino)bispropionitrile or 3-[2-(3-aminopropylamino)ethylamino]-propionitrile to N,N'-bis(3-aminopropyl)ethylenediamine.

Particularly preferred ω-aminonitriles are aminocapronitrile for preparation of hexamethylenediamine and caprolactam.

Further particularly preferred nitriles are what are called "Strecker nitriles", such as iminodiacetonitrile for preparation of diethylenetriamine and aminoacetonitrile (AAN) for preparation of ethylenediamine (EDA) and diethylenetriamine (DETA).

A preferred trinitrile is trisacetonitrile amine.

In a particularly preferred embodiment, N,N-dimethylaminopropionitrile (DMAPN) is used in the process of the invention for preparation of N,N-dimethylaminopropylamine (DMAPA).

In a further particularly preferred embodiment, isophoronenitrile imine is used in the process of the invention for preparation of isophoronediamine and, in a further particularly preferred embodiment, adiponitrile (ADN) is used to prepare hexamethylenediamine (HMD) or to prepare 6-aminocapronitrile (6-ACN) and HMD.

The nitriles used for the hydrogenation may comprise 0.01% to 10%, preferably 0.1% to 8%, more preferably 0.1% to 5% and most preferably 0.1% to 3% by weight of water. This water may originate, for example, from the process for preparing the nitriles used.

The hydrogenation as such, i.e. the reduction of the nitrile function of the nitrile used to obtain the corresponding amine function, can in principle be conducted by any methods known to those skilled in the art.

Reducing agents used for the hydrogenation may be hydrogen or a hydrogen-comprising gas. The hydrogen is generally used in technical grade purity. The hydrogen may also be used in the form of a hydrogen-comprising gas, i.e. in mixtures with other inert gases such as nitrogen, helium, neon, argon or carbon dioxide. Hydrogen-comprising gases used may, for example, be reformer offgases, refinery gases, etc., if and when these gases do not comprise any catalyst poisons for the hydrogenation catalysts used, for example CO. Preference is given, however, to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

According to the invention, the hydrogenation is conducted in an apparatus (V1) in which, as well as the reactants (nitrile and reducing agent), the further components more particularly specified below (unsupported cobalt catalyst and the compound (1)) are present.

Apparatuses (V1) used may in principle be any apparatuses which are suitable for the hydrogenation and are known to those skilled in the art. The apparatus (V1) may in principle be just one single apparatus, but it is also possible to use two or more apparatuses of this kind connected in parallel and/or in series.

The process of the invention is preferably conducted in a reactor as apparatus (V1). It is additionally preferable that, in the apparatus (V1), especially in the reactor, the unsupported cobalt catalyst is arranged in the form of a fixed bed.

In a preferred embodiment, the fixed bed arrangement comprises a catalyst bed in the actual sense, i.e. loose, supported or unsupported shaped bodies preferably in the geometry or shape described hereinafter.

For this purpose, the shaped bodies are introduced into the reactor.

In order that the shaped bodies remain in the reactor and do not fall through it, a grid base or a gas- and liquid-permeable metal sheet is typically used, on which the shaped bodies rest.

The shaped bodies both at the inlet and at the outlet of the reactor may be surrounded by an inert material. Inert materials used are generally shaped bodies which have a similar geometry to the shaped catalyst bodies described above but have inert behavior in the reaction, for example Pall rings, spheres of an inert material (e.g. ceramic, steatite, aluminum).

Alternatively, the shaped bodies may be mixed with inert material and introduced into the reactor as a mixture.

The catalyst bed (shaped bodies+any inert material) preferably has a bulk density (to EN ISO 6) in the range from 0.1 to 3 kg/L, preferably from 1.5 to 2.5 kg/L and especially preferably 1.7 to 2.2 kg/L auf.

The pressure differential across the bed is preferably less than 1000 mbar/m, preferably less than 800 mbar/m and more preferably less than 700 mbar/m. Preferably, the pressure differential across the bed is in the range from 10 to 1000 mbar/m, preferably 50 to 800 mbar/m, more preferably 100 to 700 mbar/m and especially in the range from 200 to 500 mbar/m.

In trickle mode (liquid flow direction from the top downward), the pressure differential is calculated from the pressure measured above the catalyst bed and the pressure measured below the catalyst bed.

In liquid phase mode (liquid flow direction from the bottom upward), the pressure differential is calculated from the pressure measured below the catalyst bed and the pressure measured above the catalyst bed.

Suitable fixed bed reactors are described, for example, in the article "Fixed-Bed Reactors" (Ullmann's Encyclopedia of Industrial Chemistry, published online: Jun. 15, 2000, DOI: 10.1002/14356007.b04_199).

Preference is given to conducting the process in a shaft reactor, shell and tube reactor or tubular reactor as apparatus (V1).

Particular preference is given to conducting the process in a tubular reactor.

The reactors may each be used as an individual reactor, as a series of individual reactors and/or in the form of two or more parallel reactors.

The specific reactor construction and the conduct of the reaction may vary depending on the hydrogenation process to be conducted, the reaction times required and the nature of the catalyst used.

Preferably, the ratio of height to diameter of the reactor, especially of a tubular reactor, is 1:1 to 500:1, more preferably 2:1 to 100:1 and especially preferably 5:1 to 50:1.

The flow direction of the reactants (starting materials, hydrogen, any liquid ammonia) is generally from the top downward or from the bottom upward.

More preferably, the flow direction of the reactants (starting materials, hydrogen, any liquid ammonia) is from the top downward through the reactor.

The catalyst space velocity in continuous mode is typically 0.01 to 10 kg of reactant per L of catalyst and hour, preferably from 0.2 to 5 kg of reactant per L of catalyst and hour, more preferably from 0.2 to 4 kg of reactant per L of catalyst and hour and most preferably 0.2 to 2 kg of reactant per L of catalyst and hour.

According to the invention, the superficial velocity is in the range from 5 kg/(m's) to 50 kg/(m²s), preferably in the range from 8 to 25 kg/(m²s), more preferably in the range from 10 to 20 kg/(m's) and especially preferably in the range from 12 to 18 kg/(m²s).

The superficial velocity v [kg/(m²s)] is defined as $$v = \frac{Q}{A}$$

where Q is the mass flow [kg/s] and A is the cross-sectional area of the empty reactor [m²].

The mass flow Q is in turn defined as the sum total of the masses of all the reactant streams and recycle streams supplied. Hydrogen, cycle gases and any inert gases supplied are not used to calculate the mass flow, since hydrogen, cycle gases and inert gases are generally present in the gas phase under the standard hydrogenation conditions.

In order to achieve high superficial velocities, a portion of the output (partial output) from the hydrogenation reactor is preferably recycled into the reactor as recycle stream (circulation stream). The circulation stream can be fed back to the reactor separately, or it can more preferably be mixed with the reactants supplied and fed back to the reactor together therewith.

The ratio of circulation stream to the reactant stream supplied is preferably in the range from 0.5:1 to 250:1, more preferably in the range from 1:1 to 200:1, and especially preferably in the range from 2:1 to 180:1. When no ammonia is supplied to the process, the ratio of circulation stream to the reactant stream supplied is preferably in the upper region of the aforementioned ranges. If, in contrast, a large amount of ammonia is supplied to the process, the ratio of circulation stream to the reactant stream supplied is preferably in the lower region of the aforementioned ranges.

In a preferred embodiment of the present invention, a stream (S1) which is discharged from the apparatus (V1) comprises the primary amine and is returned at least partly to the apparatus (V1), preference being given to adding compound (I) at first to the returned portion of stream (S1) and feeding it into the apparatus (V1) as a constituent of stream (S1), particular preference being given to adding compound (I) as an aqueous solution to the returned portion of stream (S1).

In a further preferred embodiment, high superficial velocities can be achieved when the reaction is conducted in a reactor having a slim design, especially in a tubular reactor having a slim design.

The ratio of height to diameter of the reactor is therefore, as described above, preferably in the range from 1:1 to 500:1, more preferably in the range from 2:1 to 100:1 and especially preferably in the range from 5:1 to 50:1.

Unsupported cobalt catalysts as such are known to those skilled in the art. In principle, it is possible in the process of the invention to use any known unsupported cobalt catalysts. Preference is given to using a single unsupported cobalt catalyst; it is optionally also possible to use mixtures of two or more different unsupported cobalt catalysts. According to the invention, it is preferable that the unsupported cobalt catalyst is used in the apparatus (V1) as a fixed bed catalyst.

Preferably, Raney cobalt catalysts, cobalt catalysts based on monoliths or cobalt catalysts based on an $LiCoO_2$ precursor are not regarded as unsupported cobalt catalysts in the context of the present invention.

Characteristic features of the unsupported cobalt catalysts used in the process of the invention are firstly that they
i) have a high proportion of catalytically active composition (active component),
ii) have a relatively low surface area and/or
iii) have a zero or only relatively small proportion of inert support material.

In other words, this means that the unsupported cobalt catalysts consist mainly of catalytically active composition (active component). The catalytically active composition is especially cobalt, where further elements, especially metals, may also be present alongside cobalt as catalytically active composition. In general, the cobalt content of the catalytically active composition is at least 55% by weight and may be up to 100% by weight (the corresponding catalysts contain only cobalt as catalytically active composition). Preferably, the cobalt content in the catalytically active composition is at least 80% by weight, especially at least 90% by weight. It is additionally preferable that the upper limit of catalytically active composition in the unsupported cobalt catalysts is 95% by weight. The remaining 5% by weight of catalytically active composition is thus formed by other elements, especially by promoters such as manganese, sodium and/or phosphorus.

In addition, it is preferable in accordance with the invention that the unsupported cobalt catalyst consists of catalytically active composition to an extent of at least 70% by weight, preferably to an extent of at least 80% by weight, more preferably to an extent of at least 90% by weight, and most preferably to an extent of at least 95% by weight.

It is additionally preferable that the unsupported cobalt catalyst comprises, as catalytically active composition, component i) and optionally components ii) and/or iii), with:
i) cobalt (Co),
ii) optionally at least one further element selected from iron (Fe), nickel (Ni), ruthenium (Ru), rhodium (Rh), palladium (Pd), osmium (Os), iridium (Ir) and platinum (Pt), and/or
iii) optionally at least one promoter selected from chromium (Cr), manganese (Mn), molybdenum (Mo), titanium (Ti), zinc (Zn), tin (Sn), alkali metals, alkaline earth metals, rare earth metals and phosphorus (P).

In a further preferred embodiment of the present invention, the catalytically active composition of the unsupported cobalt catalyst consists of 55% to 98% by weight of cobalt, 0.2% to 15% by weight of phosphorus, 0.2% to 15% by weight of manganese and 0.2% to 15% by weight of alkali metal (calculated as CoO, $H_3PO_4$, $MnO_2$ or alkali metal oxide prior to reduction with hydrogen). Preferably, the unsupported cobalt catalyst is prepared by calcining the catalyst composition in a first step at final temperatures of 550 to 750° C. and in a second step at final temperatures of 800 to 1000° C. Catalysts of this kind are known, for example, from EP-A 0 636 409. In addition, it is preferable in accordance with the invention that the unsupported cobalt catalyst
i) has a surface area of not more than 50 $m^2/g$, preferably of not more than 40 $m^2/g$, more preferably of not more than 30 $m^2/g$, and/or
ii) the proportion of support material is not more than 10% by weight (based on the total mass of the catalyst), preferably not more than 5% by weight, more preferably not more than 1% by weight, the unsupported cobalt catalyst especially being free of support material.

If the unsupported cobalt catalysts used in the process of the invention comprise a support material, it is preferably $ZrO_2$. By contrast, in accordance with the invention, support materials based on aluminas are preferably avoided.

In the process of the invention, it is also possible to use catalysts which are prepared by reducing so-called catalyst precursors.

The catalyst precursor comprises an active composition comprising one or more catalytically active components, any promoters and optionally a support material.

The catalytically active components (composition) comprise oxygen compounds of the abovementioned metals, for example the metal oxides, carbonates or hydroxides thereof, such as CoO, NiO, CuO and/or mixed oxides thereof.

In the context of this application, the expression "catalytically active component" is used for the abovementioned oxygen-containing metal compounds, but is not supposed to imply that these oxygen compounds are already catalytically active in themselves. The catalytically active components generally have catalytic activity in the conversion of the invention only after they have been reduced.

The doping elements (promoters) are preferably present in amounts of not more than 10% by weight, for example of 0.1% to 10% by weight, more preferably in amounts of 1% to 5% by weight, based in each case on the particular catalyst precursor.

Preferred catalysts comprise 50% to 99% by weight, preferably 70% to 99% by weight and more preferably 90% to 99% by weight of cobalt.

Preference is given to catalyst precursors such as the oxide mixtures which are disclosed in EP-A 0 636 409 and which comprise, prior to reduction with hydrogen, 55% to 98% by weight of Co, calculated as CoO, 0.2% to 15% by weight of phosphorus, calculated as $H_3PO_4$, 0.2% to 15% by weight of manganese, calculated as $MnO_2$, and 0.2% to 5.0% by weight of alkali metal, calculated as $M_2O$ (M=alkali metal), and Co/Mn/P catalysts prepared according to DE 34 03 377 A1, or oxide mixtures which are disclosed in EP-A-0 742 045 and comprise, prior to reduction with hydrogen, 55% to 98% by weight of Co, calculated as CoO, 0.2% to 15% by weight of phosphorus, calculated as $H_3PO_4$, 0.2% to 15% by weight of manganese, calculated as $MnO_2$, and 0.05% to 5% by weight of alkali metal, calculated as $M_2O$ (M=alkali metal) or the oxide mixtures which are disclosed in EP-A 963 975 and which comprise, prior to reduction with hydrogen, 22% to 45% by weight of $ZrO_2$, 1% to 30% by weight of oxygen compounds of copper, calculated as CuO, 15% to 50% by weight of oxygen compounds of nickel, calculated as NiO, where the molar Ni:Cu ratio is greater than 1, 15% to 50% by weight of oxygen compounds of cobalt, calculated as CoO, 0 to 10% by weight of oxygen compounds of aluminum and/or manganese, calculated as $Al_2O_3$ and $MnO_2$ respectively, and no oxygen compounds of molybdenum, for example the catalyst A disclosed in loc. cit., page 17, with the composition of 33% by weight of Zr, calculated as $ZrO_2$, 28% by weight of Ni, calculated as NiO, 11% by weight of Cu, calculated as CuO and 28% by weight of Co, calculated as CoO, or the oxide mixtures which are disclosed in EP 445 589 B1 and which comprise, prior to reduction, 65% by weight of CoO, 4.7% by weight of $Mn_3O_4$, 10% by weight of CaO, or 69% by weight of CoO, 4.9% by weight of $Mn_3O_4$, 5.5% by weight of NiO, 10.4% by weight of $Fe_2O_3$ and 10.0% by weight of CaO.

Suitable shaped bodies are shaped bodies having any desired geometry and shape. Preferred shapes are tablets, rings, cylinders, star extrudates, strand shapes, wagonwheels or spheres, particular preference being given to tablets, rings, cylinders, strand shapes, spheres or star extrudates. Very particular preference is given to strand shapes or tablets.

In the case of spheres, the diameter of the sphere shape is preferably 10 mm or less, more preferably 4 mm or less, even more preferably 3 mm or less and especially preferably 2.5 mm or less.

In a preferred embodiment, in the case of spheres, the diameter of the sphere shape is preferably in the range from 0.1 to 10 mm, more preferably in the range from 0.5 to 4 mm, even more preferably in the range from 1 to 3 mm and especially preferably in the range from 1.5 to 2.5 mm.

In the case of strands or cylinders, the ratio of length: diameter is preferably in the range from 1:1 to 20:1, more preferably 1:1 to 14:1, even more preferably in the range from 1:1 to 10:1 and especially preferably in the range from 1:2 to 6:1.

The diameter of the strands or cylinders is preferably 10 mm or less, more preferably 5 mm or less, even more preferably 3 mm or less and especially preferably 2.5 mm or less.

In a preferred embodiment, the diameter of the strands or cylinders is preferably in the range from 0.1 to 10 mm, more preferably in the range from 0.5 to 3 mm, even more preferably in the range from 1 to 2.5 mm and especially preferably in the range from 1.5 to 2.5 mm.

In the case of tablets, the height h of the tablet is preferably 10 mm or less, more preferably 4 mm or less, even more preferably 3 mm or less and especially preferably 2.5 mm or less.

In a preferred embodiment, the height h of the tablet is preferably in the range from 0.1 to 10 mm, more preferably in the range from 0.5 to 4 mm, even more preferably in the range from 1 to 3 mm and especially preferably in the range from 1.5 to 2.5 mm. The ratio of height h (or thickness) of the tablet to the diameter D of the tablet is preferably 1:1 to 1:5, more preferably 1:1 to 1:2.5, even more preferably 1:1 to 1:2.

In all other geometries, the shaped catalyst body in the process of the invention in each case preferably has an equivalent diameter $L=1/a'$ of 2 mm or less, more preferably 1 mm or less, even more preferably 0.7 mm or less, and especially preferably 0.5 mm or less, where a' is the external surface area per unit volume ($mm_s^2/mm^3$), with:

$$a' = \frac{A_p}{V_p}$$

where $A_p$ is the external surface area of the shaped body ($mm^2$) and $V_p$ the volume of the shaped body ($mm^3$).

In a preferred embodiment, the shaped catalyst body in the process of the invention, in all other geometries, in each case preferably has an equivalent diameter $L=1/a'$ in the range from 0.1 to 2 mm, more preferably in the range from 0.1 to 0.7 mm, even more preferably in the range from 0.2 to 0.5 mm and especially preferably in the range from 0.3 to 0.4 mm.

The surface area and the volume of the shaped body are calculated from the geometric dimensions of the shaped body by the known mathematical formulae.

The volume can also be calculated by the following method, in which:
1. the internal porosity of the shaped body is determined (for example via measurement of the water absorption in [ml/g cat] at room temperature and total pressure 1 bar),
2. determining the displacement of the shaped body on immersion into a liquid (for example by gas displacement by means of a helium pycnometer) and
3. forming the sum of the two volumes.

The surface area can also be calculated theoretically by the following method, in which an envelope around the shaped body is defined, having a curve radius of max. 5 μm (in order not to embrace the internal pore surface area through "penetration" of the envelope into the pores) and being in very intimate contact with the shaped body (no intersection with the support). This could be visualized as a very thin film which is placed around the shaped body, to which a vacuum is then applied from the inside, such that the film very tightly encloses the shaped body.

The shaped body used preferably has a bulk density (to EN ISO 6) in the range from 0.1 to 3 kg/L, preferably from 1.5 to 2.5 kg/L and especially preferably 1.7 to 2.2 kg/L.

In a preferred embodiment, the catalysts are used in the process of the invention in the form of shaped bodies which are produced by impregnation of support materials which have the abovementioned geometry or which, after the impregnation, are shaped to shaped bodies having the abovementioned geometry.

Examples of useful support materials include carbon, such as graphite, carbon black, graphene, carbon nanotubes and/or activated carbon, alumina (gamma, delta, theta, alpha, kappa, chi or mixtures thereof), silicon dioxide, zirconium dioxide, zeolites, aluminosilicates or mixtures thereof.

The abovementioned support materials can be impregnated by the customary processes (A. B. Stiles, Catalyst Manufacture—Laboratory and Commercial Preparations, Marcel Dekker, New York, 1983), for example by application of a metal salt solution in one or more impregnation stages. Useful metal salts generally include water-soluble metal salts such as the nitrates, acetates or chlorides of the corresponding catalytically active components or doping elements, such as cobalt nitrate or cobalt chloride. Thereafter, the impregnated support material is generally dried and optionally calcined.

Calcining is performed generally at temperatures between 300 and 800° C., preferably 350 to 600° C., especially at 450 to 550° C.

The impregnation can also be effected by the "incipient wetness method", in which the support material is moistened with the impregnation solution up to a maximum of saturation, according to its water absorption capacity. Alternatively, impregnation may take place in supernatant solution.

In the case of multistage impregnation processes, it is appropriate to dry and optionally to calcine between individual impregnation steps. Multistage impregnation should be employed advantageously when the support material is to be contacted with metal salts in a relatively large amount.

For the purpose of applying a plurality of metal components to the support material, impregnation may take place simultaneously with all of the metal salts, or in any desired order of the individual metal salts in succession.

Preference is given to using support materials which already have the above-described preferred geometry of the shaped bodies.

However, it is also possible to use support materials present in the form of powder or spall, and to subject impregnated support materials to shaping.

For example, the impregnated and dried or calcined support material can be conditioned.

The conditioning can be effected, for example, by adjusting the impregnated support material to a particular particle size by grinding. After grinding, the conditioned, impregnated support material can be mixed with shaping aids such as graphite or stearic acid, and processed further to give shaped bodies.

Standard processes for shaping are described, for example, in Ullmann's Encyclopedia Electronic Release 2000, chapter: "Catalysis and Catalysts", pages 28-32 and by Ertl et al. (Ertl, Knözinger, Weitkamp, Handbook of Heterogeneous Catalysis, VCH Weinheim, 1997, pages 98 ff.).

Standard processes for shaping are, for example, extrusion, tableting, i.e. mechanical pressing, or pelletizing, i.e. compaction by circular and/or rotating movements.

The shaping operation can give shaped bodies with the abovementioned geometry.

The conditioning or shaping is generally followed by a heat treatment. The temperatures in the heat treatment typically correspond to the temperatures in the calcination.

In a preferred embodiment, shaped bodies which are produced by coprecipitation of all the components thereof, the catalyst precursors thus precipitated being subjected to a shaping operation, are used in the process of the invention.

For this purpose, a soluble compound of the corresponding active component, the doping elements and optionally a soluble compound of a support material in a liquid is admixed while heating and stirring with a precipitant until precipitation is complete.

The liquid used is generally water.

Useful soluble compounds of the active components typically include the corresponding metal salts, such as the nitrates, sulfates, acetates or chlorides, of the aforementioned metals.

The soluble compounds of a support material used are generally water-soluble compounds of Ti, Al, Zr, Si etc., for example the water-soluble nitrates, sulfates, acetates or chlorides of these elements.

The soluble compounds of the doping elements used are generally water-soluble compounds of the doping elements, for example the water-soluble nitrates, sulfates, acetates or chlorides of these elements.

In a further preferred embodiment, the shaped bodies can be produced by precipitative application.

Precipitative application is understood to mean a production method in which a sparingly soluble or insoluble support material is suspended in a liquid and then soluble compounds, such as soluble metal salts, of the corresponding metal oxides are added, and these are then precipitated onto the suspended support by addition of a precipitant (for example, described in EP-A2 1 106 600, page 4, and A. B. Stiles, Catalyst Manufacture, Marcel Dekker, Inc., 1983, page 15).

Examples of useful sparingly soluble or insoluble support materials include carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally in the form of powder or spall.

The liquid used, in which the support material is suspended, is typically water.

Useful soluble compounds include the aforementioned soluble compounds of the active components or of the doping elements.

Typically, in the precipitation reactions, the soluble compounds are precipitated as sparingly soluble or insoluble, basic salts by addition of a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., particularly 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals used. With regard to the filterability of the precipitates, it may prove to be favorable for them to be aged, meaning that they are left alone for a certain time after precipitation, optionally under hot conditions or with air being passed through.

The precipitates obtained by these precipitation processes are typically processed, by washing, drying, calcining and conditioning them.

After washing, the precipitates are generally dried at 80 to 200° C., preferably 100 to 150° C., and then calcined.

Calcining is performed generally at temperatures between 300 and 800° C., preferably 350 to 600° C., especially at 450 to 550° C.

After the calcination, the pulverulent catalyst precursors obtained by precipitation reactions are typically conditioned.

The conditioning can be effected, for example, by adjusting the precipitation catalyst to a particular particle size by grinding.

After grinding, the catalyst precursor obtained by precipitation reactions can be mixed with shaping aids such as graphite or stearic acid and processed further to give shaped bodies.

Standard processes for shaping are described, for example, in Ullmann's Encyclopedia Electronic Release 2000, chapter: "Catalysis and Catalysts", pages 28-32 and by Ertl et al. (Ertl, Knözinger, Weitkamp, Handbook of Heterogeneous Catalysis, VCH Weinheim, 1997, pages 98 ff.).

Standard processes for shaping are, for example, extrusion, tableting, i.e. mechanical pressing, or pelletizing, i.e. compaction by circular and/or rotating movements.

The shaping operation can give shaped bodies having the abovementioned geometry.

The conditioning or shaping is generally followed by a heat treatment. The temperatures in the heat treatment typically correspond to the temperatures in the calcination.

Shaped bodies which have been produced by impregnation or precipitation comprise the catalytically active components, after calcination, generally in the form of the oxygen compounds thereof, for example as the metal oxides or hydroxides thereof, such as CoO, NiO, CuO and/or the mixed oxides thereof (catalyst precursors).

The catalyst precursors which have been prepared as described above by impregnation or precipitation are generally reduced after the calcination or conditioning. The reduction generally converts the catalyst precursor to the catalytically active form thereof.

The reduction of the catalyst precursor can be performed at elevated temperature in an agitated or unagitated reduction furnace.

The reducing agent used is typically hydrogen or a hydrogen-comprising gas.

The hydrogen is generally used in technical grade purity. The hydrogen can also be used in the form of a hydrogen-comprising gas, i.e. in mixtures with other inert gases, such as nitrogen, helium, neon, argon or carbon dioxide. The hydrogen stream can also be recycled in the reduction as cycle gas, optionally mixed with fresh hydrogen and optionally after removal of water by condensation.

The catalyst precursor is preferably reduced in a reactor in which the shaped bodies are arranged as a fixed bed. Particular preference is given to reducing the catalyst precursor in the same reactor in which the subsequent reaction of the nitriles with hydrogen is effected.

In addition, the catalyst precursor can be reduced in a fluidized bed reactor in the fluidized bed.

The catalyst precursor is generally reduced at reduction temperatures of 50 to 600° C., especially from 100 to 500° C., more preferably from 150 to 450° C.

The partial hydrogen pressure is generally from 1 to 300 bar, especially from 1 to 200 bar, more preferably from 1 to 100 bar, the pressure figures here and hereinafter relating to the pressure measured in absolute terms.

The duration of the reduction is preferably 1 to 20 hours, and more preferably 5 to 15 hours.

During the reduction, a solvent can be supplied in order to remove water of reaction formed and/or in order, for example, to be able to heat the reactor more quickly and/or to be able to better remove the heat during the reduction. The solvent here may also be supplied in supercritical form.

Suitable solvents used may be the above-described solvents. Preferred solvents are water or ethers such as methyl tert-butyl ether, ethyl tert-butyl ether, dioxane or tetrahydrofuran. Particular preference is given to water or tetrahydrofuran. Suitable solvents likewise include suitable mixtures.

The shaped body thus obtained, after reduction, can be handled under inert conditions. The shaped body can preferably be handled and stored under an inert gas such as nitrogen, or under an inert liquid, for example an alcohol, water or the product of the particular reaction for which the catalyst is used. In that case, it may be necessary to free the catalyst of the inert liquid prior to commencement of the actual reaction.

Storage of the catalyst under inert substances enables uncomplicated and nonhazardous handling and storage of the shaped body.

After reduction, the shaped body can also be contacted with an oxygen-comprising gas stream such as air or a mixture of air with nitrogen.

In this way, a passivated shaped body is obtained. The passivated shaped body generally has a protective oxide layer. This protective oxide layer simplifies the handling and storage of the catalyst, such that, for example, the installation of the passivated shaped body into the reactor is simplified. A passivated shaped body is preferably reduced as described above by treatment of the passivated catalyst with hydrogen or a hydrogen-comprising gas prior to contacting with the reactants. The reduction conditions generally correspond to the reduction conditions which are employed in the course of reduction of the catalyst precursors. The activation generally removes the protective passivation layer. More preferably, the at least one compound (I) is added repeatedly or continuously to the apparatus (V1) during the hydrogenation.

According to the invention, at least one compound (I) is thus added recurrently or continuously to the apparatus (V1)—i.e. the hydrogenation. The compound (I) comprises at least one component selected from alkali metal, alkaline earth metal and rare earth metal. The compound (I) is known as such to those skilled in the art. Preferably, one compound (I) is added recurrently or continuously to the apparatus (V1); it is optionally also possible to add mixtures of two or more compounds (I). In addition, it is possible that at least one compound (I) is already present in the apparatus (V1) prior to commencement of the hydrogenation, but preference is given to adding the compound (I) to the process of the invention only after commencement of the hydrogenation.

The addition of at least one compound (I) to the apparatus (V1) may, as already explained, be recurrent or continuous. At the same time, the compound (I) can be added in liquid or solid form. It should also be emphasized here that the compound (I) need not be added directly to the apparatus (V1); instead, the compound (I) may first also be added in another apparatus, for example in a contacting apparatus (V2), to one or more of the components involved in the hydrogenation. From this other apparatus, the compound (I) is conducted into the apparatus (V1) (indirect addition the compound (I) to (V1)). The conduction/transfer or passage of the compound (I) from the other apparatus into the apparatus (V1) is effected by the methods known to those skilled in the art, for example using pumps. More particularly, the compound (I), as already explained above, can be added to a returned portion of stream (S1).

In the context of the present invention, a "continuous addition" of the compound (I) is understood to mean that the corresponding addition is effected over a prolonged period, preferably over at least 50% of, more preferably over at least 70% of, even more preferably over at least 90% of and especially over the entire reaction time. Preferably, the continuous addition is conducted in such a way that the appropriate apparatus (V1) for introduction (addition) of the compound (I) (for example a star feeder) is in operation over the aforementioned periods.

In the context of the present invention, a "recurrent addition" of the compound (I) is understood to mean that the corresponding addition is effected at regular or irregular time intervals. Preferably, the corresponding addition is occasioned by the occurrence of a condition of addition described further down, especially in connection with the concentration of the compound (I) in the output from the apparatus (V1). The time intervals between the individual additions are at least 1 h, preferably at least one day. In the context of the present invention, the term "recurrent" is additionally understood to mean at least two, for example 3, 4, 5, 10 or even 100, individual additions. The specific number of individual additions depends on the operating period. The latter ideally tends toward infinity.

In other words, a recurrent addition of the compound (I), in the context of the present invention, is understood to mean the mutually delimited additions of several batches of compound (I). The addition of a single batch may take from several seconds to several minutes; as the case may be, even somewhat longer periods are conceivable. According to the invention, the time interval between the respective additions of an individual batch is at least ten times as long as the duration of addition of the corresponding batch. As the case may be, in the context of the present invention, the embodiment of a "recurrent addition" may also be combined together with the embodiment of a "continuous addition".

The exact dosage of the recurrent or continuous addition of at least one compound (I) is illustrated by way of example hereinafter by the addition of lithium hydroxide.

However, the details also apply mutatis mutandis to all other compounds covered by the definition of the compound (I) of the present invention.

The lithium concentration in the output should not go below a certain threshold value. If the concentration does go lower, this is an indicator that lithium has been leached out of the catalyst.

The lithium concentration in the output should not be too high either, since the catalyst otherwise loses its activity (poisoning).

The metered addition can also be effected continuously or recurrently (periodically). What is essential is that the lithium concentration in the output/reaction mixture does not become so high as to result in deposits, but is sufficiently high that the concentration on the catalyst is maintained.

More particularly, particular requirements also apply to the site of metered addition:

The lithium concentration of the solution metered in must not be too high, since there will otherwise be deposits/blockages in the reactor.

The feeding should be undertaken at a point in the reactor where there is a high flow rate, in order that the LiOH mixes well with the reaction mixture. LiOH has a low solubility in water and in most organic solvents.

Useful compounds (I) of the alkali metals include Li compounds, Na compounds, K compounds, Rb compounds and Cs compounds, useful compounds (I) of the alkaline earth metals include Mg compounds, Ca compounds, Sr compounds and Ba compounds, and useful compounds (I) of the rare earth metals include La compounds, Ce compounds, Pr compounds and Nd compounds.

Preferred compounds (I) of the alkali metals are lithium, potassium and cesium, preferred compounds (I) of the alkaline earth metals are magnesium and calcium, and preferred compounds (I) of the rare earth metals are lanthanum and cerium.

It is additionally preferable that the compound (I) is used in the form of an oxide, a hydroxide and/or a salt, and/or that the compound (I) is used in the form of an aqueous solution. Useful salts include, for example, nitrates, carbonates, hydrogencarbonates, phosphates and carboxylates, for example formates and acetates. Preference is given to hydroxides, which are not covered by the term "salts" in the context of the present invention.

It is additionally preferable that an aqueous solution of an oxide, a hydroxide or a salt of lithium, of potassium, of cesium, of magnesium, of calcium, of lanthanum and/or cerium is used.

Very particular preference is given to aqueous solutions of compounds of lithium, for example lithium hydroxide, lithium carbonate, lithium phosphate, lithium nitrate, lithium formate, lithium acetate. Preference is given here to lithium hydroxide, and so an aqueous solution of lithium hydroxide is especially preferred.

Solvents used for alkali metal, alkaline earth metal and rare earth compounds may in principle be organic solvents, water or mixtures of these solvents with water. Preference is given to the solvents which are also mentioned further down as solvents for the nitriles used. They have to be stable under the hydrogenation conditions and dissolve the alkali metal, alkaline earth metal and rare earth compounds to a sufficient degree.

Preference is therefore given to $C_1$ to $C_4$ alcohols, water or mixtures of these compounds. Very particular preference is given to water.

It is additionally preferable in accordance with the invention that i) the nitrile used for hydrogenation comprises 0.01% to 10% by weight of water, and/or ii) the compound (I) is added to the apparatus (V1) as soon as the proportion of secondary amine formed as by-product is greater than 0.5 GC area %, and/or iii) added to the hydrogenation mixture in the apparatus (V1) via the addition of the compound (I) is 0.01 to 500 ppm of alkali metal, alkaline earth metal and/or rare earth metal, based on g-atoms of nitrile in the apparatus (V1), preference being given to adding to the hydrogenation mixture in the apparatus (V1) via the addition of the compound (I) 0.01 to 500 ppm of alkali metal, alkaline earth metal and/or rare earth metal, based on g-atoms of nitrile in the apparatus (V1), as soon as the proportion of secondary amine formed as by-product in the apparatus (V1) is greater than 0.5 GC area %, at a catalyst space velocity of 0.01 to 10 kg of reactant per L of catalyst and hour.

"g-atoms of nitrile in the apparatus (V1)" is understood in the context of the present invention to mean the total amount (the total weight) in grams (g) of nitrile in the apparatus (V1).

It is thus preferable in accordance with the invention that 0.01 to 500 ppm of alkali metal, alkaline earth metal and/or rare earth metal, based on the total weight in grams of nitrile in the apparatus (V1), is added to the hydrogenation mixture in the apparatus (V1) via the addition of the compound (I), preference being given to adding 0.01 to 500 ppm of alkali metal, alkaline earth metal and/or rare earth metal, based on the total weight in grams of nitrile in the apparatus (V1), to the hydrogenation mixture in the apparatus (V1) via the addition of the compound (I) as soon as the proportion of secondary amine formed as by-product in the apparatus (V1) is greater than 0.5 GC area %, at a catalyst space velocity of 0.01 to 10 kg of reactant per L of catalyst and hour.

Methods of determining GC area % are known as such to those skilled in the art. Preferably, the GC area percentages are measured with the following parameters: GC column: 60 m CP Volamine/WCOT fused silica 0.32; temperature program: 50° C.-10 min-15° C./min-240° C.-30 min.

According to the invention, the hydrogenation can be conducted batchwise, semicontinuously, but preferably continuously.

The hydrogenation is generally conducted at a pressure of 1 to 300 bar, especially of 5 to 150 bar, preferably of 10 to 100 bar and more preferably of 15 to 60 bar. Most preferably, the hydrogenation is executed at a pressure of less than 60 bar as a low-pressure process.

The temperature is generally within a range from 25 to 300° C., especially from 50 to 200° C., preferably from 70 to 150° C., more preferably from 80 to 140° C.

The molar ratio of hydrogen to nitrile used is generally 2:1 to 25:1, preferably 2:1 to 10:1. The hydrogen can be recycled into the reaction as cycle gas.

At the same time, the reaction conditions are preferably selected such that the nitriles used and liquids added are generally in the liquid phase and only the hydrogen used or inert gases are in the gas phase under the reaction conditions mentioned.

The outcome of the hydrogenation, in the case of continuous performance in particular, can be monitored analytically, for example by gas chromatography. If the analysis reveals a drop in the selectivity for primary amine with formation of secondary amine, for example bis-DMAPA, as by-product, this drop can preferably be reversed by adding the solutions mentioned.

The compound (I) is metered in as soon as the proportion of secondary amine formed is greater than 0.5 GC area %, preferably greater than 1 GC area %, more preferably greater than 2 GC area %, even more preferably greater than 5 GC area %, especially greater than 10 GC area %.

The hydrogenation can be conducted in substance or in a liquid.

Suitable solvents are, for example, C1 to C4 alcohols such as methanol or ethanol, C4 to C12 dialkyl ethers such as diethyl ether or tert-butyl methyl ether, or cyclic C4 to C12 ethers such as tetrahydrofuran or dioxane, or hydrocarbons such as pentane, hexane, heptane, octane, cyclohexane. Suitable solvents may also be mixtures of the aforementioned liquids. In a preferred embodiment, the solvent is a product of the hydrogenation.

The workup of the hydrogenation outputs is preferably effected by distillation. This removes the added alkali metal, alkaline earth metal and/or rare earth compounds as bottom products.

In addition, it is preferable in accordance with the invention that the hydrogenation is conducted in the absence of ammonia. When the ammonia-free mode of operation is selected, the pressure in the hydrogenation is preferably <85 bar. If, in contrast, the hydrogenation is effected in the presence of ammonia, it is likewise possible to observe an additional improvement with regard to the nitrile conversion and the selectivity for the primary amine. Moreover, ammonia contributes to removal of the heat of hydrogenation.

In addition, it is preferable in accordance with the invention that the apparatus (V1) is a reactor, the superficial velocity preferably being 5 to 50 kg of mass flow per $m^2$ of cross-sectional area of the reactor and second.

The present invention is illustrated hereinafter by examples.

EXAMPLE 1

Hydrogenation of Dimethylaminopropionitrile (DMAPN) to Dimethylaminopropylamine (DMAPA) in the Presence of an Unsupported Cobalt Catalyst with Recurrent Supply of Aqueous Lithium Hydroxide Solution a) Catalyst Preparation and Activation The catalyst used is an unsupported cobalt catalyst composed of 90.4% by weight of cobalt, 5.1% by weight of manganese, 0.3% by weight of sodium and 3.1% by weight of phosphorus (strand diameter 2 mm), which is produced according to example 1 of EP-A 636 409. 40.2 g of this catalyst are introduced into a hydrogenation reactor and heated up to 280° C. with supply of 25 L (STP) of hydrogen per hour within 12 hours, kept at this temperature while feeding in 25 L (STP) of hydrogen per hour for 12 hours and cooled under hydrogen.

b) Hydrogenation of DMAPN

The hydrogenation is conducted in trickle mode with the above-described catalyst as fixed bed catalyst in a stainless steel tubular reactor (1.4571 inner tube) having a height of one meter and a diameter of 0.6 cm. The reaction output from the hydrogenation is cooled, decompressed, partly discharged and partly recycled into the reactor.

The feedstock used for the hydrogenation is technical grade DMAPN comprising dimethylamine and water. According to GC analysis, the water content is 0.3 to 3.6 area %, the dimethylamine content 1.4 to 2.5 area % (GC column: 60 m CP Volamine/WCOT fused silica 0.32; temperature program: 50° C.-10 min-15° C./min.-240° C.-30 min).

The hydrogenation is conducted for a total of 4000 hours, for the first 149 hours without addition of aqueous LiOH solution, then for 3800 hours with intermittent addition of LiOH solution. Table 1 compiles the addition times and amounts of LiOH; table 2 shows the lithium concentration in the reactor output.

TABLE 1

Metered addition of lithium hydroxide

| Start [h] | End [h] | Duration [h][1] | Concentration[2] | Amount [g/h][3] | DMAPN [g/h] | Space velocity[4] [kg/Lh] | ppm [LiOH/DMAPN][5] | ppm [Li/DMAPN][6] | LiOH absolute [g][7] |
|---|---|---|---|---|---|---|---|---|---|
| 149 | 320 | 171 | 1.00% | 0.0665 | 19.4 | 1.00 | 34.29 | 9.94 | 0.1138 |
| 794 | 915 | 121 | 1.00% | 0.0665 | 19.4 | 1.00 | 34.29 | 9.94 | 0.0803 |
| 1155 | 1270 | 115 | 1.00% | 0.0665 | 19.4 | 1.00 | 34.29 | 9.94 | 0.0762 |
| 1511 | 1845 | 334 | 0.10% | 0.3326 | 19.4 | 1.00 | 17.14 | 4.97 | 0.1110 |
| 1845 | 1968 | 123 | 0.20% | 0.3326 | 19.4 | 1.00 | 34.29 | 9.94 | 0.0820 |
| 1973 | 2159 | 186 | 0.50% | 0.3326 | 19.4 | 1.00 | 85.71 | 24.85 | 0.3097 |
| 2159 | 2181 | 22 | 1.00% | 0.3326 | 19.4 | 1.00 | 171.43 | 49.70 | 0.0726 |
| 2304 | 2379 | 75 | 1.00% | 0.3326 | 19.4 | 1.00 | 171.43 | 49.70 | 0.2494 |
| 2449 | 2541 | 93 | 1.00% | 0.3326 | 19.4 | 1.00 | 171.43 | 49.70 | 0.3079 |
| 2541 | 2668 | 127 | 1.00% | 0.3326 | 19.4 | 0.95 | 171.43 | 49.70 | 0.4208 |
| 2668 | 3116 | 448 | 1.00% | 0.3497 | 20.4 | 1.00 | 171.43 | 49.70 | 1.5678 |
| 3311 | 3621 | 311 | 1.00% | 0.3497 | 20.4 | 1.00 | 171.43 | 49.70 | 1.0863 |

[1]Duration of addition of the aqueous lithium hydroxide solution
[2]Lithium hydroxide concentration of the aqueous lithium hydroxide solution
[3]Amount of the aqueous lithium hydroxide solution
[4]Kilograms of DMAPN/liter of catalyst and hour
[5]Ratio of lithium hydroxide to DMAPN (g/g)
[6]Ratio of lithium to DMAPN (g/g)
[7]Absolute amount of lithium hydroxide which has been run into the reactors within the particular addition interval.

The hydrogenation is started by pumping 200 mL of crude DMAPA into the reactor.

The hydrogenation temperature is 90 to 110° C.; the pressure is 85 bar for the first 700 hours, then 50 bar for the rest of the run time.

The catalyst space velocity over the entire run time is 1 to 1.1 kg DMAPN per liter of catalyst and hour. The superficial velocity is 41 to 42 kg per m² and hour. In order to attain these values, a portion of the hydrogenation output is returned to the reactor after decompression.

Between 2544 and 3500 hours of run time, DMAPN comprising 5% by weight of water is employed.

Over the first 149 hours of hydrogenation time without addition of aqueous LiOH solution, the hydrogenation output contains only 87% to 90% DMAPA, 11% to 13% bis-DMAPA and 0.2% to 0.3% DMAPN (GC area %); see also comparative example 2, operation without ammonium.

After 149 hours, the first metered addition of aqueous LiOH solution is commenced (metering periods specified in table 1). After addition of aqueous LiOH solution, the DMAPN conversion from 200 hours after the start of the experiment onward is at least 99.4% over the remaining 3500 hours. The DMAPA yields are 99.1% to 99.5%. The only by-product that occurs is bis-DMAPA in amounts of 0.2% to 0.9%.

Figure 2:
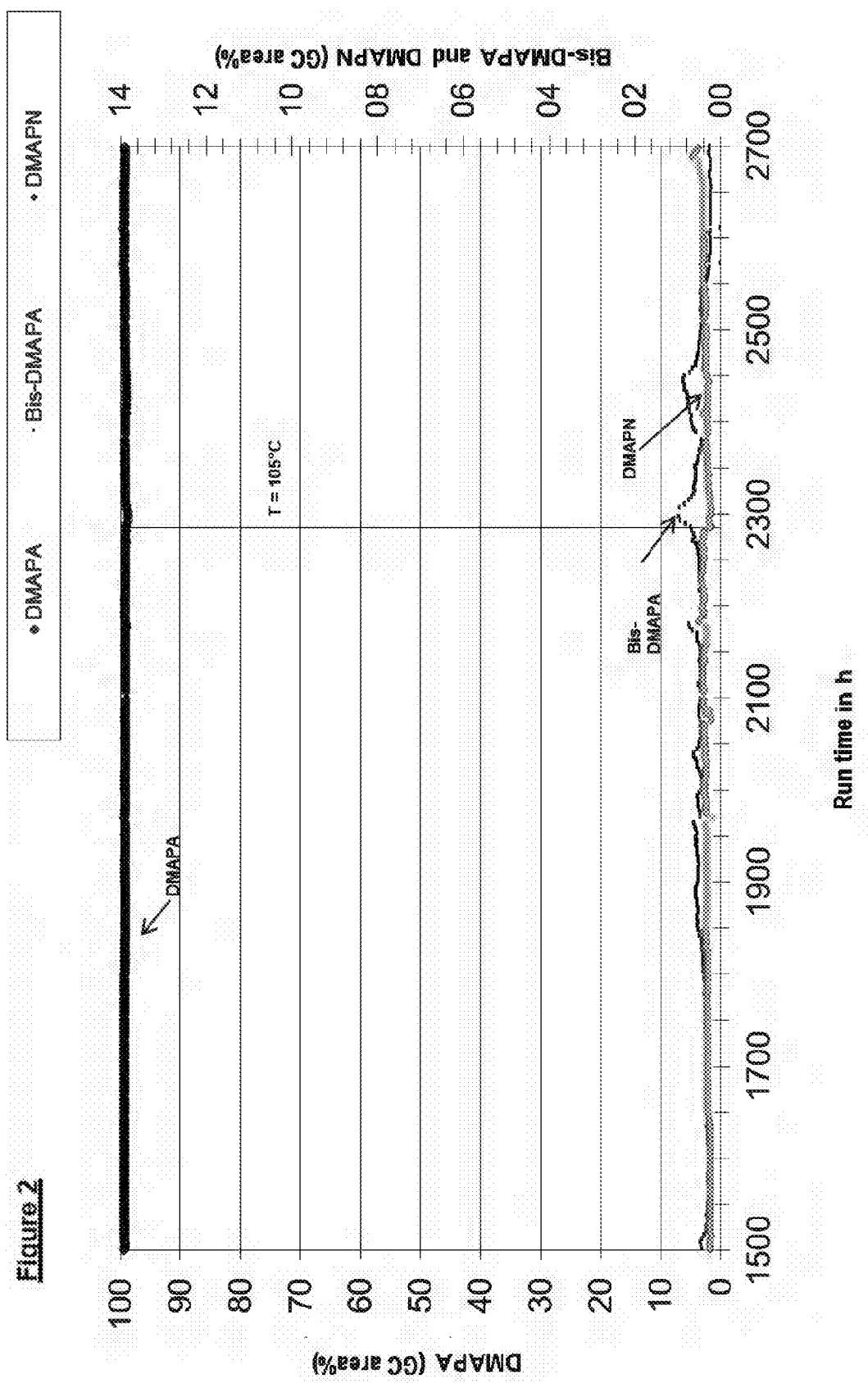
Figure 3:
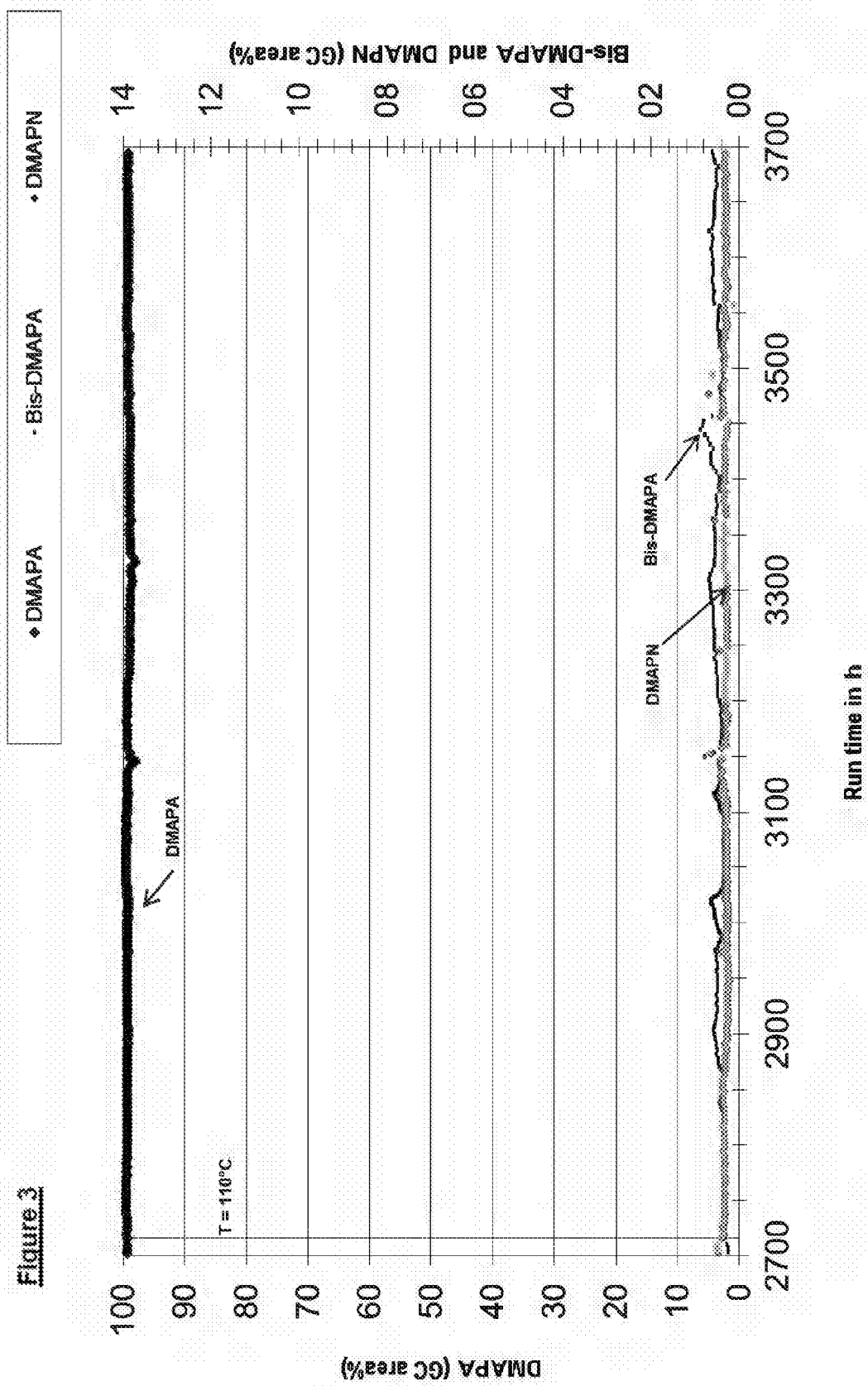

As example 1 shows, rising or high bis-DMAPA values during operation without metered addition of LiOH can be lowered again to a lower level by addition of LiOH. In this regard, FIGS. 1 to 3 show the concentrations of reactant (DMAPN), lithium hydroxide, product (DMAPA) and by-product (bis-DMAPA) measured in the reaction output over the entire experimental duration of example 1.

Example 1 additionally shows that the positive effects with small amounts of LiOH are achievable, that it is possible to work with high catalyst space velocities combined with high catalyst service lives, and that water in the hydrogenation mixture is not disruptive. Moreover, high DMAPN conversions and DMAPA yields are achieved, and it is possible to work in the absence of ammonia.

TABLE 2

Determination of lithium concentration in the output

| Run time [h] | Lithium content of output [ppm] |
| --- | --- |
| 172 | 14.0 |
| 246 | 7.0 |
| 270 | 17.0 |
| 294 | 10.0 |
| 316 | 12.0 |
| 342 | 2.8 |
| 414 | 1.4 |
| 438 | 1.6 |
| 486 | 1.1 |
| 510 | 0.9 |
| 580 | 1.1 |
| 654 | 0.8 |
| 772 | 0.7 |
| 172 | 14.0 |
| 825 | 22.0 |
| 846 | 17.0 |
| 963 | 2.4 |
| 988 | 2.2 |
| 1007 | 3.0 |
| 1031 | 2.4 |
| 1127 | 1.6 |
| 1201 | 20.0 |
| 1609 | 16.0 |
| 1775 | 2.0 |
| 1825 | 1.8 |
| 1871 | 1.8 |
| 1967 | 8.9 |
| 2039 | 1.8 |
| 2117 | 2.8 |
| 2188 | 74.0 |
| 2303 | 3.0 |
| 2351 | 5.0 |
| 2447 | 2.7 |
| 2543 | 10.0 |
| 2615 | 9.0 |
| 2669 | 11.0 |
| 2711 | 11.0 |
| 2813 | 9.0 |
| 3005 | 10.0 |
| 3052 | 9.0 |
| 3143 | 14.0 |
| 3215 | 8.0 |
| 3293 | 4.0 |
| 3337 | 6.0 |
| 3509 | 11.0 |
| 3629 | 11.0 |

COMPARATIVE EXAMPLE 2

Figure 4:
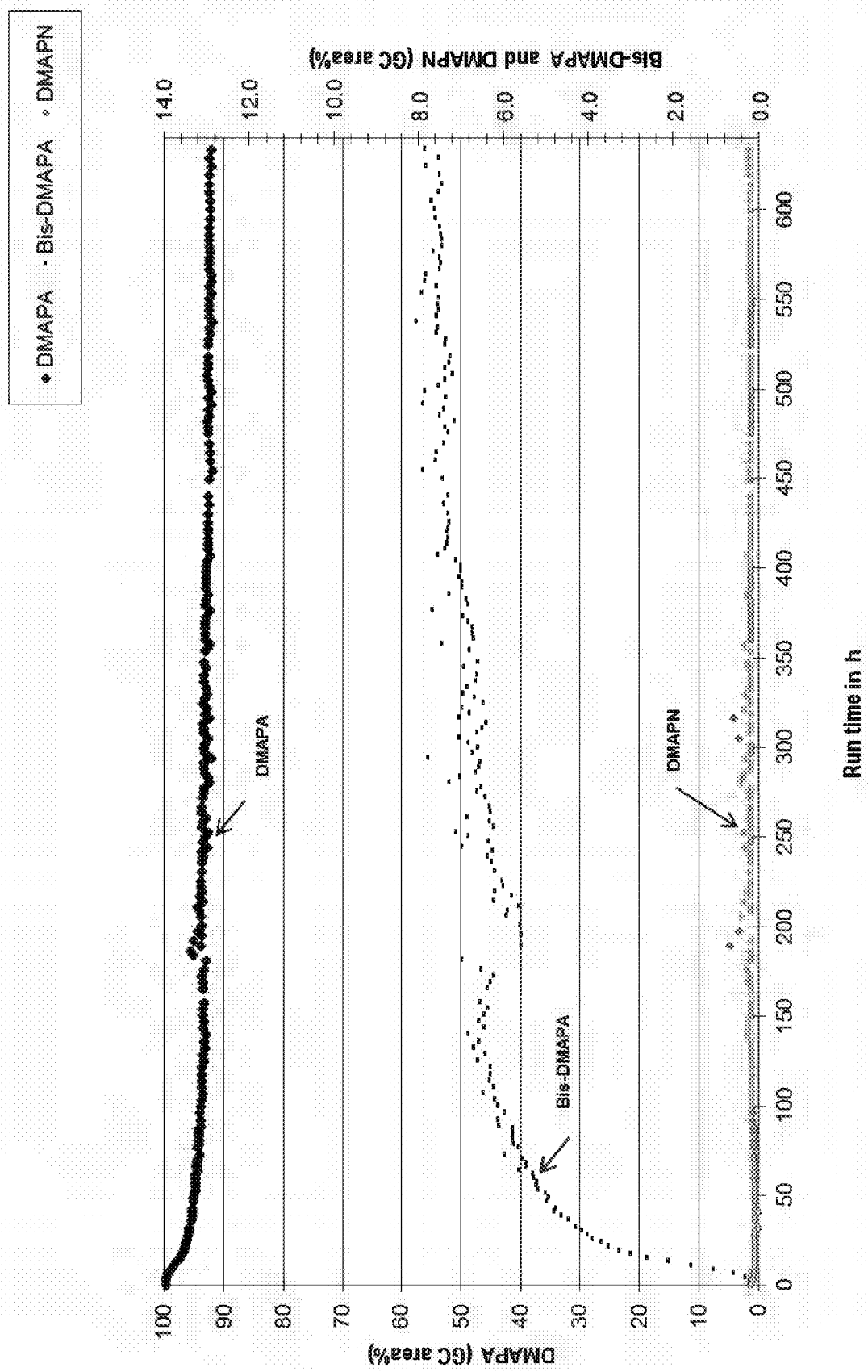

Hydrogenation of DMAPN to DMAPA in the Presence of a Cobalt Catalyst with Initial Single Impregnation of the Catalyst with Aqueous LiOH Solution 40.2 g of the catalyst charge used in example 1 are activated as described and the catalyst in the plant is flushed through with about 400 g of a 10% aqueous LiOH solution in straight pass from the bottom upward (1 mL/minute). About 7 hours after commencement of the feed of LiOH solution, in addition, the liquid circuit is switched on with a recycle rate of 1000 g/L for 2 hours, then the recycling and the metered addition of LiOH are switched off again. Subsequently, the desired reaction conditions are established (90° C., hydrogen) and the plant is started up with DMAPA. A liquid recycle rate of 814 g/h and a DMAPN feed rate of 19.4 g/h are established. The catalyst thus pretreated, as described in example 1, is used for the hydrogenation of DMAPN at 90° C. and 85 bar. The lithium concentration in the reaction output is determined regularly. After 500 hours of reaction time, the hydrogenation output consists to an extent of about 92% of DMAPA, about 8% of bis-DMAPA and less than about 0.5% of DMAPN (GC area %). Analogously to FIGS. 1 to 3 for example 1, the corresponding values for comparative example 2 are illustrated in FIG. 4.

Comparative example 2 shows that, in the case of unsupported cobalt catalysts in a fixed bed, by contrast with Raney cobalt (catalyst in suspension mode; see, for example, example 50 from EP-A 913 388), a pretreatment of the catalyst with LiOH does not bring about any increase in selectivity. The regular determination of lithium in the reaction output shows that the lithium is washed continuously out of the plant and off the catalyst. This effect is visible in comparative example 2, especially in about the first 200 hours after commencement of the hydrogenation. The reduction in selectivity with regard to DMAPA and the increase in bis-DMAPA correlate with the amount of lithium washed out of the reactor. Up to the end of the experiment after about 650 hours, the selectivity for DMAPA continues to decrease continuously and lithium is still detectable in the reaction output.

COMPARATIVE EXAMPLE 3

Hydrogenation of DMAPN to DMAPA in the Presence of an Unsupported Cobalt Catalyst and of Ammonia and in the Absence of Ammonia (without Lithium Hydroxide Addition)

40.2 g of the catalyst charge used in example 1 are activated as described. Analogously to example 1, the plant is first started up with 200 mL of crude DMAPA. A temperature of 90° C. and a pressure of 85 bar are established and maintained over the duration of the experiment. 16 g/h of ammonia and 25 L (STP)/h of hydrogen are metered in continuously; the hydrogenation is started by feeding in 19.4 g/h of DMAPN.

The catalyst space velocity over the entire run time is 1 to 1.1 kg of DMAPN per liter of catalyst and hour. The superficial velocity is 34 to 42 kg per $m^2$ and hour. In order to achieve these values, a portion of the hydrogenation output is returned to the reactor after decompression. After a reaction time of 301 hours, the hydrogenation output consists to an extent of 97.8% of DMAPA and less than about 0.3% of DMAPN; bis-DMAPA is not present (GC area %).

After 312 hours, under otherwise unchanged experimental conditions, the ammonia feed is stopped. The selectivity for DMAPA achieved is much lower in the absence of ammonia. After a reaction time of 442 hours, the hydrogenation output consists to an extent of 85.9% of DMAPA, less than about 0.3% of DMAPN, and 11.1% of bis-DMAPA (GC area %).

Figure 5:
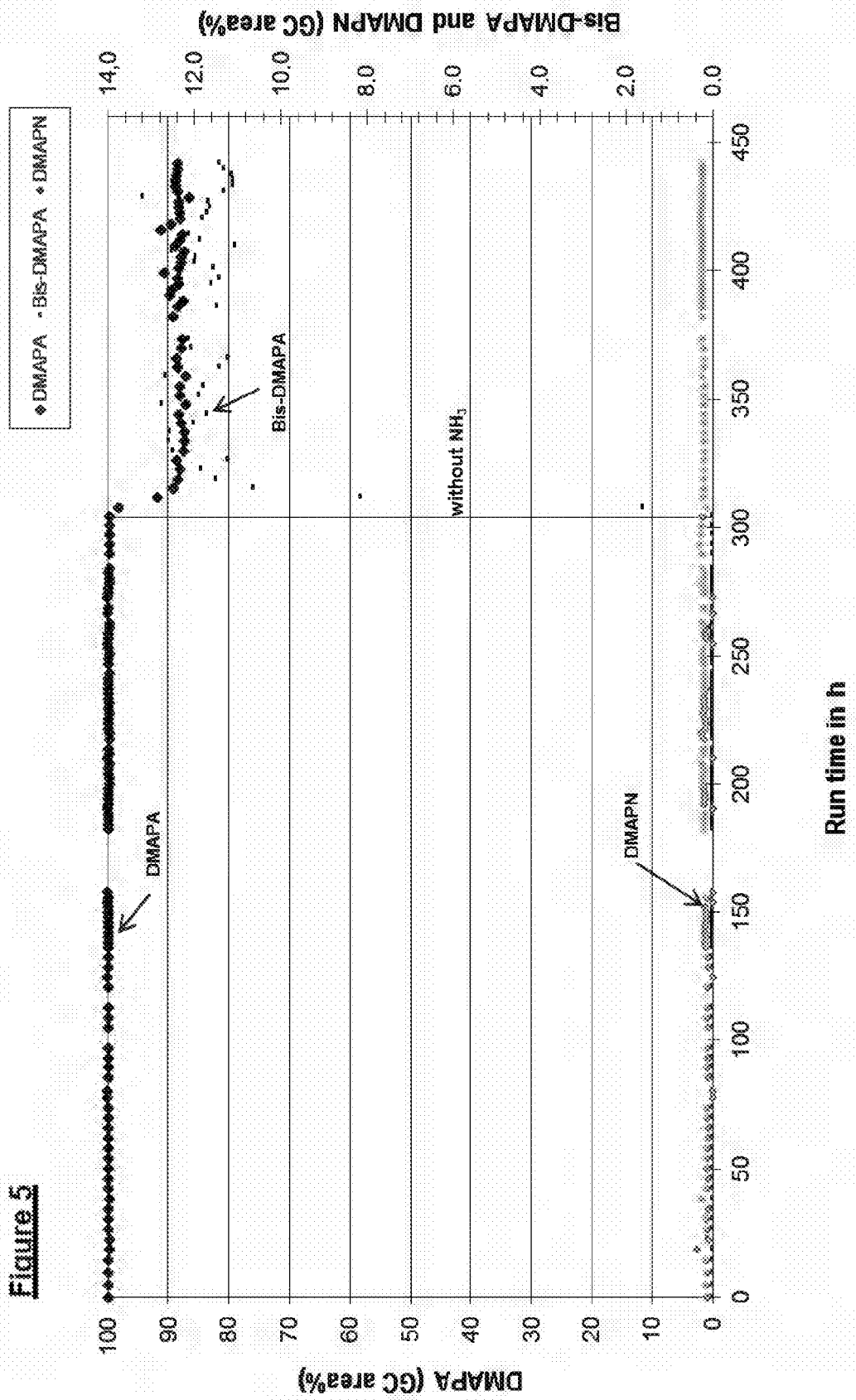

Comparative example 3 shows that large amounts of bis-DMAPA are formed over the unsupported cobalt catalyst studied in the absence of ammonia at 85 bar, and the selectivity for DMAPA is low. In the presence of ammonia, because of the vapor pressure of ammonia, a distinct drop in the reaction pressure is not possible. The corresponding concentration values according to comparative example 3 are illustrated analogously to the previous examples in FIG. 5.

The invention claimed is:

1. A process for preparing a primary amine, the process comprising:
   hydrogenating at least one nitrile in an apparatus (V1) in the presence of an unsupported cobalt catalyst to obtain at least one primary amine, with recurrent or continuous addition of at least one compound (I) to the apparatus (V1),
   wherein said compound (I) comprises at least one component selected from the group consisting of an alkali metal, an alkaline earth metal, and a rare earth metal.

2. The process according to claim 1, wherein said compound (I) is an oxide, a hydroxide, a salt, or an aqueous solution.

3. The process according to claim 2, wherein said compound (I) is an aqueous solution of an oxide, a hydroxide or a salt of lithium, potassium, cesium, magnesium, calcium, lanthanum, or cerium.

4. The process according to claim 2, wherein said compound (I) is an aqueous solution of lithium hydroxide.

5. The process according to claim 1, wherein
   i) the nitrile comprises 0.01% to 10% by weight of water, or
   ii) the compound (I) is added to the apparatus (V1) as soon as a proportion of a secondary amine formed as a by-product is greater than 0.5 GC area %, or
   iii) added to the apparatus (V1) via the addition of the compound (I) is 0.01 to 500 ppm of an alkali metal, an alkaline earth metal, or a rare earth metal, based on g atoms of nitrile in the apparatus (V1), as soon as the proportion of the secondary amine formed as the by-product in the apparatus (V1) is greater than 0.5 GC area %, at a catalyst space velocity of 0.01 to 10 kg of reactant per L of catalyst and hour.

6. The process according to claim 1, wherein the hydrogenating is conducted in the absence of ammonia.

7. The process according to claim wherein
   the apparatus (V1) is a reactor, and
   a superficial velocity being 5 to 50 kg of mass flow per $m^2$ of cross-sectional reactor area and second.

8. The process according to claim 1, wherein the hydrogenating is conducted at a pressure of 1 to 300 bar.

9. The process according to claim 1, wherein the unsupported cobalt catalyst is used in the apparatus (V1) as a fixed bed catalyst.

10. The process according to claim 1, wherein the nitrile is an aliphatic mono-, di- or trinitrile, a cycloaliphatic mono- or dinitrile, an alpha-, beta- or omega-aminonitrile, or an alkoxynitrile.

11. The process according to claim 1, wherein
    the at least one primary amine is N,N-dimethylaminopropylamine (DMAPA) and the nitrile is N,N-dimethyl-aminopropionitrile (DMAPN), or
    the at least one primary amine is isophoronediamine and the nitrile is isophoronenitrileimine, or
    the at least one primary amine is hexamethylenediamine (HMD) or 6-aminocapronitrile (6-ACN) and HMD, and the nitrile is adiponitrile (ADN).

12. The process according to claim 1, wherein the unsupported cobalt catalyst consists of catalytically active composition to an extent of at least 70% by weight.

13. The process according to claim 1, wherein the unsupported cobalt catalyst comprises, as catalytically active composition:
    i) cobalt (Co),
    ii) optionally at least one element selected from the group consisting of iron (Fe), nickel (Ni), ruthenium (Ru), rhodium (Rh), palladium (Pd), osmium (Os), iridium (Ir), and platinum (Pt), or
    iii) optionally at least one promoter selected from the group, consisting of chromium (Cr), manganese (Mn), molybdenum (Mo), titanium (Ti), zinc (Zn), tin (Sn), an alkali metal, an alkaline earth metal, a rare earth metal, and phosphorus (P).

14. The process according to claim 13, wherein the catalytically active composition of the unsupported cobalt catalyst consists of 55% to 98% by weight of cobalt, 0.2% to 15% by weight of phosphorus, 02% to 15% by weight of manganese, and 0.2% to 15% by weight of an alkali metal, calculated as CoO, $H_3PO_4$, $MnO_2$, and an alkali metal oxide prior to reduction with hydrogen, respectively.

15. The process according to claim 14, wherein the unsupported cobalt catalyst is prepared by calcining the catalytically active composition first at a final temperature of 550 to 750° C. and then at a final temperature of 800 to 1000° C.

16. The process according to claim 1, wherein the unsupported cobalt catalyst
    i) has surface area of not more than 50 $m^2$/g, or
    ii) a proportion of support material is not more than 10% by weight, based on a total mass of the catalyst.

17. The process according to claim 16, wherein the unsupported cobalt catalyst
    i) has a surface area of not more than 40 $m^2$/g, or
    ii) a proportion of the support material is not more than 5% by weight, based on the total mass of the catalyst.

18. The process according to claim 1, wherein a stream (S1) which is discharged from the apparatus (V1) comprises the primary amine and is returned at least partly to the apparatus (V1).

19. The process according to claim 18, wherein the compound (I) is added at first to the returned portion of the stream (S1) and then fed into the apparatus (V1) as a constituent of the stream (S1).

20. The process according to claim 18, wherein the compound (I) is added as an aqueous solution to the returned portion of the stream (S1).

21. The process according to claim 1, wherein the unsupported cobalt catalyst consists of catalytically active composition to an extent of at least 80% by weight.

\* \* \* \* \*